(12) United States Patent
Perticone et al.

(10) Patent No.: US 11,640,706 B2
(45) Date of Patent: *May 2, 2023

(54) SYSTEMS AND METHODS FOR IMAGE PROCESSING

(71) Applicant: Leidos Security Detection & Automation, Inc., Tewksbury, MA (US)

(72) Inventors: David Perticone, Winchester, MA (US); Andrew D. Foland, Wellesley, MA (US)

(73) Assignee: Leidos Security Detection & Automation, Inc., Tewksbury, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/093,326

(22) Filed: Nov. 9, 2020

(65) Prior Publication Data

US 2021/0056677 A1 Feb. 25, 2021

Related U.S. Application Data

(63) Continuation of application No. 15/986,422, filed on May 22, 2018, now Pat. No. 10,832,391.

(Continued)

(51) Int. Cl.
*G06K 9/00* (2022.01)
*G06T 7/00* (2017.01)
(Continued)

(52) U.S. Cl.
CPC .......... *G06T 7/0002* (2013.01); *G06K 9/6256* (2013.01); *G06N 3/08* (2013.01);
(Continued)

(58) Field of Classification Search
CPC ................... G06K 9/6256; G06N 3/08; G06T 2207/10116; G06T 2207/20081;
(Continued)

(56) References Cited

U.S. PATENT DOCUMENTS 7,260,173 B2 8/2007 Wakayama et al.
8,180,139 B2 5/2012 Basu
(Continued)

FOREIGN PATENT DOCUMENTS

GB 2454782 A 5/2009
JP 2004-177138 A 6/2004
(Continued)

OTHER PUBLICATIONS

Akcay et al., Transfer Learning Using Convolutional Neural Networks for Object Classification Within X-ray Baggage Security Imagery. IEEE, International Conference on Image Processing (ICIP). pp. 1057-1061, Sep. 25-28, 2016.
(Continued)

*Primary Examiner* — Xin Jia
(74) *Attorney, Agent, or Firm* — McCarter & English, LLP

(57) ABSTRACT

A computing-device implemented system and method for identifying an item in an x-ray image is described. The method includes training a machine learning algorithm with at least one training data set of x-ray images to generate at least one machine-learned model. The method further includes receiving at least one rendered x-ray image that includes an item, identifying the item using the at least one model, and generating an automated detection indication associated with the item.

21 Claims, 10 Drawing Sheets

Related U.S. Application Data

(60) Provisional application No. 62/509,676, filed on May 22, 2017.

(51) Int. Cl.
| | | |
|---|---|---|
| *G06N 3/08* | (2023.01) | |
| *G16H 30/20* | (2018.01) | |
| *G06K 9/62* | (2022.01) | |
| *G06T 7/73* | (2017.01) | |
| *G08B 13/189* | (2006.01) | |
| *G06V 20/00* | (2022.01) | |

(52) U.S. Cl.
CPC ............... *G06T 7/73* (2017.01); *G06V 20/00* (2022.01); *G08B 13/189* (2013.01); *G16H 30/20* (2018.01); *G06T 2207/10116* (2013.01); *G06T 2207/20081* (2013.01); *G06T 2207/20084* (2013.01); *G06T 2207/30112* (2013.01); *G06V 2201/05* (2022.01)

(58) Field of Classification Search
CPC . G06T 2207/20084; G06T 2207/30112; G06T 7/0002; G06T 7/73; G06V 20/00; G06V 2201/05; G08B 13/189; G16H 30/20
See application file for complete search history.

(56) References Cited

U.S. PATENT DOCUMENTS

| | | | |
|---|---|---|---|
| 8,290,230 | B2 | 10/2012 | Chen et al. |
| 10,832,391 | B2 | 11/2020 | Perticone et al. |
| 2004/0101097 | A1 | 5/2004 | Wakayama et al. |
| 2011/0206240 | A1 | 8/2011 | Hong et al. |
| 2012/0243741 | A1* | 9/2012 | Shet ..................... G06K 9/6296 382/103 |
| 2013/0327948 | A1 | 12/2013 | Bendahan et al. |
| 2017/0242148 | A1 | 8/2017 | Yu et al. |
| 2018/0032857 | A1 | 2/2018 | Lele et al. |
| 2018/0089531 | A1* | 3/2018 | Geva ........................ G06F 3/015 |
| 2020/0051017 | A1 | 2/2020 | Dujmic |

FOREIGN PATENT DOCUMENTS

| | | |
|---|---|---|
| JP | 2009-122108 A | 6/2009 |
| JP | 2010-230676 A | 10/2010 |
| JP | 2010-540930 A | 12/2010 |
| WO | 2009/045616 A2 | 4/2009 |

OTHER PUBLICATIONS

Gregory et al., Deep Learning Technical Intterchange. Transportation Security Administration. Slideshow, 16 pages, Aug. 22-23, 2017.

Hinton et al., Reducing the dimensionality of data with neural networks. Science. Jul. 2, 2006;313(5786):504-7.

Jaccard et al., Automated detection of smuggled high-risk security threats using Deep Learning. Cornell University, retrieved online at: https://arxiv.org/abs/1609.02805. 7 pages, Sep. 9, 2016.

Jaccard et al., Tackling the X-ray cargo inspection challenge using machine learning. Proceedings Anomaly Detection and Imaging with X-rays (ADIX). 2016;9847:89470N-1-98470N-13.

Jaccard et al., Using deep learning on X-ray images to detect threats. Defence and Security Doctoral Symposium Paper, 16 pages. May 18, 2016.

Mikolov et al., Efficient Estimation of Word Representations in Vector Space. Cornell University, retrieved online at: https://arxiv.org/abs/1301.3781v3. 12 pages, Sep. 7, 2013.

Perticone et al., Initial Results on Deep Convolutional Neural Network Classification of Trimat Images. 4 pages, Oct. 14, 2016.

Perticone, DHS Deep Learning Technical Interchange: Vendor Perspective. 1 page, Aug. 22-23, 2017.

Rogers et al., A deep learning framework for the automated inspection of complex dual-energy x-ray cargo imagery. Proceedings of SPIE, Anomaly Detection and Imaging with X-rays (ADIX) II. May 1, 2017;10187:101870L, 12 pages.

Strellis, Duke—Rapiscan Initial Successes, Deep Learning Technical Exchange. Transportation Security Admiinistration. Slideshow 12 pages, Aug. 22-23, 2017.

Suk, An Introduction to Neural Networks and Deep Learning. Deep Learning for Medical Image Analysis. Academic Press, pp. 3-24, Jan. 18, 2017.

Szegedy et al., Going deeper with convolutions. 12 pages, Sep. 14, 2014.

International Search Report and Written Opinion for Application No. PCT/US2018/033874, dated Nov. 8, 2018, 14 pages.

International Search Report and Written Opinion for Application No. PCT/US2019/046014, dated Nov. 11, 2019, 17 pages.

Japanese Office Action for Application No. 2019-564499, dated Feb. 7, 2022, 10 pages.

U.S. Appl. No. 15/986,422, filed May 22, 2018, U.S. Pat. No. 10,832,391, Issued.

U.S. Appl. No. 16/537,417, filed Aug. 9, 2019, 2020-0051017, Published.

Nam et al., Dual Attention Networks for Multimodal Reasoning and Matching. IEEE Conference on Computer Vision and Pattern Recognition. pp. 299-307, (2017).

Japanese Office Action for Application No. 2019-564499, dated Oct. 24, 2022, 6 pages.

* cited by examiner

SYSTEMS AND METHODS FOR IMAGE PROCESSING

RELATED APPLICATIONS

This application is a Continuation of U.S. patent application Ser. No. 15/986,422 filed on May 22, 2018, which claims priority to, and the benefit of, U.S. Provisional Patent Application No. 62/509,676, entitled "Systems and Methods for Image Processing", filed on May 22, 2017, the contents of each application are hereby incorporated by reference in their entirety.

BACKGROUND

Imaging technologies including x-ray computed tomography, magnetic resonance imaging (MRI), positron emission tomography (PET), and many others have found widespread use in applications as diverse as medical imaging and cargo inspection. Images of cargo are manually evaluated by security personnel for threat detection.

SUMMARY

In one embodiment, a computing-device implemented method for identifying an item in an x-ray image using at least one computing device equipped with a processor is provided. The method includes training, using the at least one computing device, a machine learning algorithm with at least one training data set of x-ray images to generate at least one machine-learned model. The at least one training data set includes a first set of x-ray images of items containing threats and a second set of x-ray images of items not containing threats. The machine learning algorithm is a convolutional neural network (CNN). The method further includes receiving, with the at least one computing device, at least one rendered x-ray image that includes an item. The method also includes identifying, with the at least one computing device, the item using the at least one model. The method further includes generating, with the at least one computing device, an automated detection indication associated with the item.

In another embodiment, a system for identifying an item in an x-ray image is provided. The system includes a scanner configured to render at least one x-ray image and a computing device equipped with a processor in communication with the scanner. The computing device is configured to train a machine learning algorithm with at least one training data set of x-ray images to generate at least one machine-learned model. The at least one training data set includes a first set of x-ray images of items containing threats and a second set of x-ray images of items not containing threats. The machine learning algorithm is a convolutional neural network (CNN). The computing device is also configured to receive the at least one rendered x-ray image from the scanner. The at least one rendered x-ray image includes an item and the computing device is further configured to identify the item using the at least one model. The computing device is also configured to generate an automated detection indication associated with the item.

In still another embodiment, a non-transitory computer readable medium storing instructions executable by a processor is provided. Execution of the instructions causes the processor to implement a method for identifying an item in an x-ray image. The method includes training a machine learning algorithm with at least one training data set of x-ray images to generate at least one machine-learned model. The at least one training data set includes a first set of x-ray images of items containing threats and a second set of x-ray images of items not containing threats. The machine learning algorithm is a convolutional neural network (CNN). The method also includes receiving at least one rendered x-ray image that includes an item. The method further includes identifying the item using the at least one model and generating an automated detection indication associated with the item.

BRIEF DESCRIPTION OF THE DRAWINGS

The skilled artisan will understand that the drawings are primarily for illustrative purposes and are not intended to limit the scope of the subject matter described herein. The drawings are not necessarily to scale; in some instances, various aspects of the subject matter disclosed herein may be shown exaggerated or enlarged in the drawings to facilitate an understanding of different features. In the drawings, like reference characters generally refer to like features (e.g., functionally similar or structurally similar elements).

The foregoing and other features and advantages provided by the present disclosure will be more fully understood from the following description of exemplary embodiments when read together with the accompanying drawings, in which.

DETAILED DESCRIPTION

Figure 1:
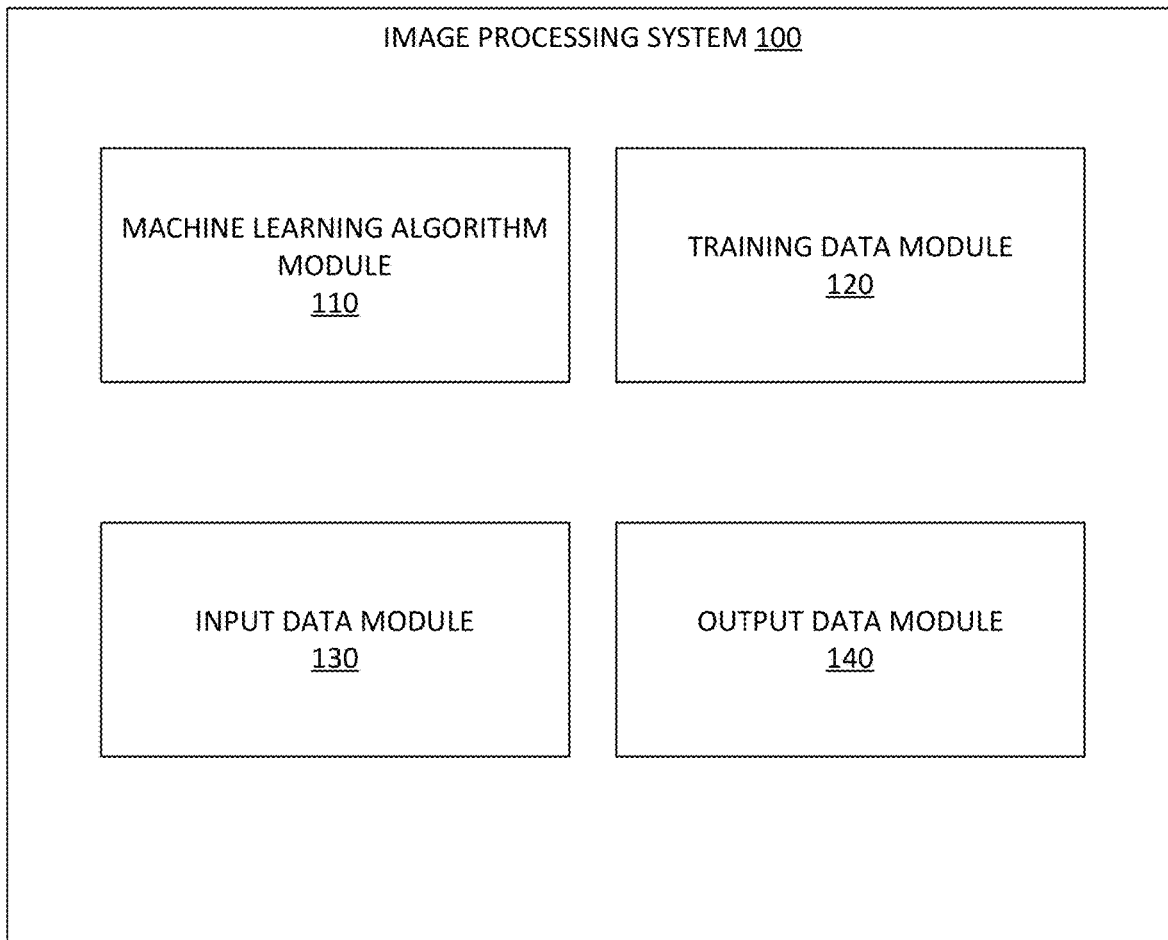
FIG. 1 is a block diagram showing an image processing system in terms of modules according to an example embodiment.

Described herein are systems, methods and computer readable media for processing images to identify an item or items in the images. Exemplary embodiments provide an image processing system that includes a machine learning framework to automatically analyze images. In some embodiments, the images consist of x-ray images that may be obtained via a scanner or screening device at a security checkpoint. The machine learning algorithm implemented in the described framework identifies a specific object type in the images (e.g., laptops, shoes, bottles, weapons, etc.) and perform a task specific to that item type. For example, the task can include threat detection in a laptop within a passenger bag or security belt bin. In an example embodiment, the systems and methods described herein may be used to make an automated decision on whether a specific item is present in the luggage or package of interest (by analyzing the x-ray image of the luggage or package), and whether the specific item, if present, includes a threat (e.g., explosive devices). In some embodiments, a label is included in an output image generated by the image processing system identifying the specific item in the analyzed image. In some embodiments, the location of the specific item is indicated or highlighted in an output image of the image processing system. In another embodiment, the systems and methods described herein may be used to visually or audibly indicate to security personnel that the luggage or package includes a specific item that includes a threat. In one embodiment, the machine learning framework employs a deep learning convolutional neural network (CNN) framework to analyze x-ray images of items, luggage, and packages.

The systems and methods described herein may be used in various security applications, such as but not limited to, where security personnel are evaluating images of items, luggage, packages or containers for threat. For example, the image processing system described herein can be used by the Transportation Security Administration (TSA) at airports for checking passengers' luggage at a security checkpoint. The image processing system may also be used by the TSA to scan passengers' checked-in luggage. The image processing system may also be used to check cargo on transport or delivery vehicles. The image processing system may also be used to check packages mailed via the postal system. In an example embodiment, the systems and methods described herein may also be used to process images produced during body x-ray scans of a passenger to identify items concealed by the passenger on or in his or her body.

In exemplary embodiments, a machine learning algorithm is executed on a machine learning framework or platform. The machine learning algorithm is trained using a training data set to analyze a specific format or type of images, for example, x-ray volumetric or projection images. A projection image of the volume may be formed directly by the rays of an x-ray system's imaging sensors, or synthetically by a mathematical summation operation on a volumetric image volume. The trained machine learning algorithm generates one or more models based on the training data set. The generated models are stored, and used to analyze one or more input images. The input images are images of items, luggage or packages obtained via an x-ray machine. As used herein, a projection image represents a superposition of all overlapping objects traversed by an incoming ray until it reaches a detector.

Based on the training data set used to train the machine learning algorithm, the image processing system is capable of identifying a specified item. For example, the training data set can include a set of images that contain a laptop and a corresponding set of images that do not contain a laptop. Such a data set is used to train the image processing system to identify, via a machine learned model, whether a laptop is in an input image. In an example embodiment, the systems and methods described herein can be used to identify whether the specified item contains an item of interest, such as a threat, an explosive, a liquid, a solid, a gas, a gel, a pressurized liquid or gas, and the like. For example, the training data set can include a set of images that include a container with a liquid and a set of images that include a container with a solid. Such a data set is used to train the image processing system to identify, via a machine learned model, whether an input image includes a container with a liquid or a container with a solid.

Figure 7:
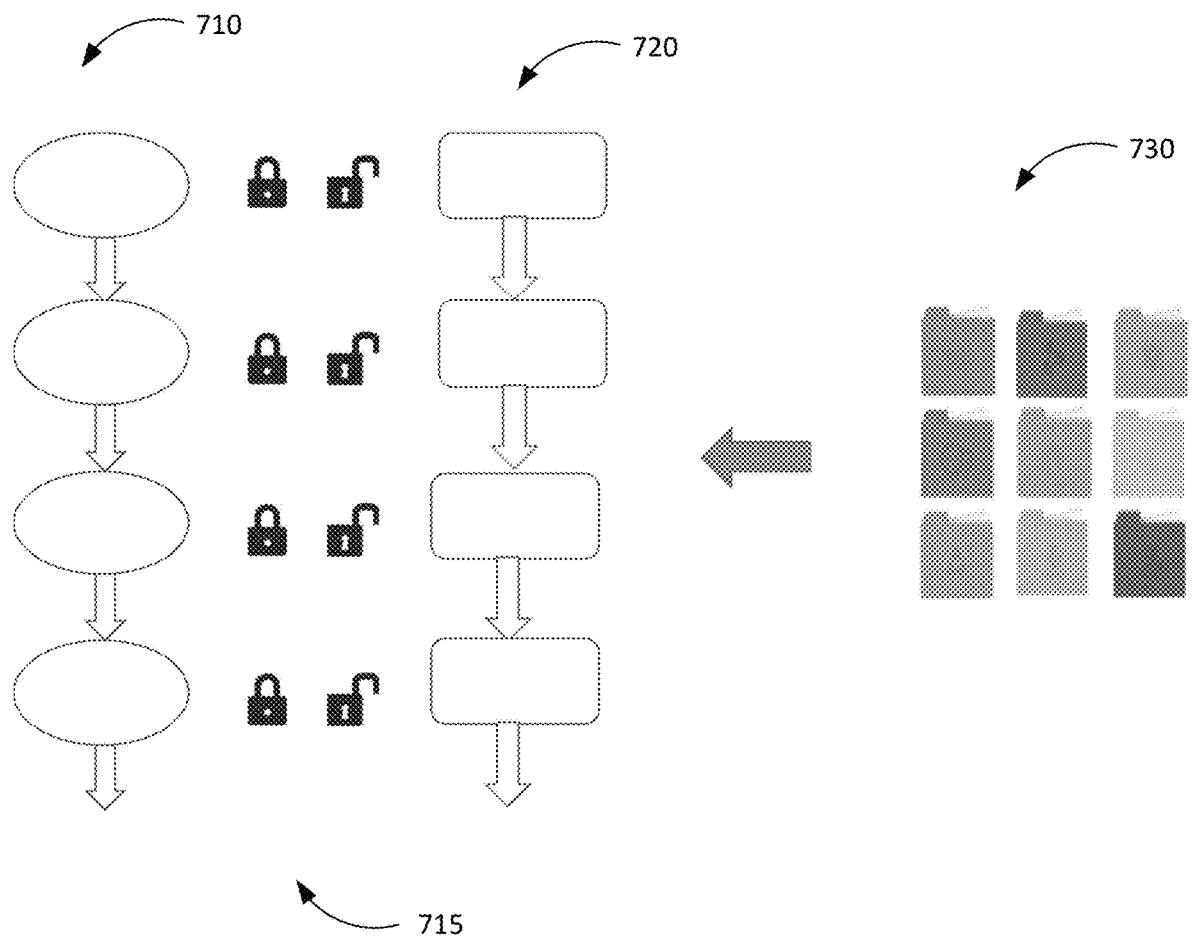
FIG. 7 schematically depicts an exemplary system for training the machine learning algorithm, according to an example embodiment.

FIG. 1 is a block diagram showing an image processing system 100 in terms of modules according to an example embodiment. One or more of the modules may be implemented using device 710, scanning device 720, server 730 and/or database 740 as shown in FIG. 7. The modules include a machine learning algorithm module 110, a training data set module 120, an input data module 130, and an output data module 140. The modules may include various circuits, circuitry and one or more software components, programs, applications, or other units of code base or instructions configured to be executed by one or more processors. In some embodiments, one or more of modules 110, 120, 130, 140 may be included in server 730, while other of the modules 110, 120, 130, 140 are provided in device 710 or scanning device 720. Although modules 110, 120, 130, and 140 are shown as distinct modules in FIG. 1, it should be understood that modules 110, 120, 130, and 140 may be implemented as fewer or more modules than illustrated. It should be understood that any of modules 110, 120, 130, and 140 may communicate with one or more components included in system 700 (FIG. 7), such as device 710, scanning device 720, server 730, or database(s) 740.

The machine learning algorithm module 110 may be a hardware-implemented module configured to execute or run a machine learning algorithm, and may store and manage parameters, variables, data and other components needed to execute the machine learning algorithm. In an example embodiment, the machine learning algorithm is a deep learning convolution neural network (here after referred to as "deep learning CNN").

The training data set module 120 may be a hardware-implemented module configured to manage and store a training data set for the machine learning algorithm employed by the image processing system 100. In an example embodiment, the training data set includes multiple images obtained using an x-ray screening machine or device of items, luggage or packages. The items may include a laptop, bottle, shoe, or other specified object. The luggage or packages may contain one or more of a laptop, bottle, shoe, or other specified items. In an example embodiment, the training data set includes multiple colorized x-ray images.

The input data module 130 may be a hardware-implemented module configured to manage and store input images that are analyzed by the image processing system 100 to identify presence of a specified object within the image.

The output data module 140 may be a hardware-implemented module configured to manage and store the output of the machine learning algorithm. In some embodiments, the output is an indication whether the input image includes a specified object, and whether the specified object includes a threat. In an example embodiment, the output is an output image indicating the presence of the specified object by visually highlighting or emphasizing the specified object in the input image. In one embodiment, the output image may include a label identifying the specified object. In another example embodiment, the output is an alarm or alert generated at a security screening machine or device to indicate to an operator or security personnel that the items, luggage or packages include a threat based on analysis of the images of respective items, luggage or packages.

Figure 2:
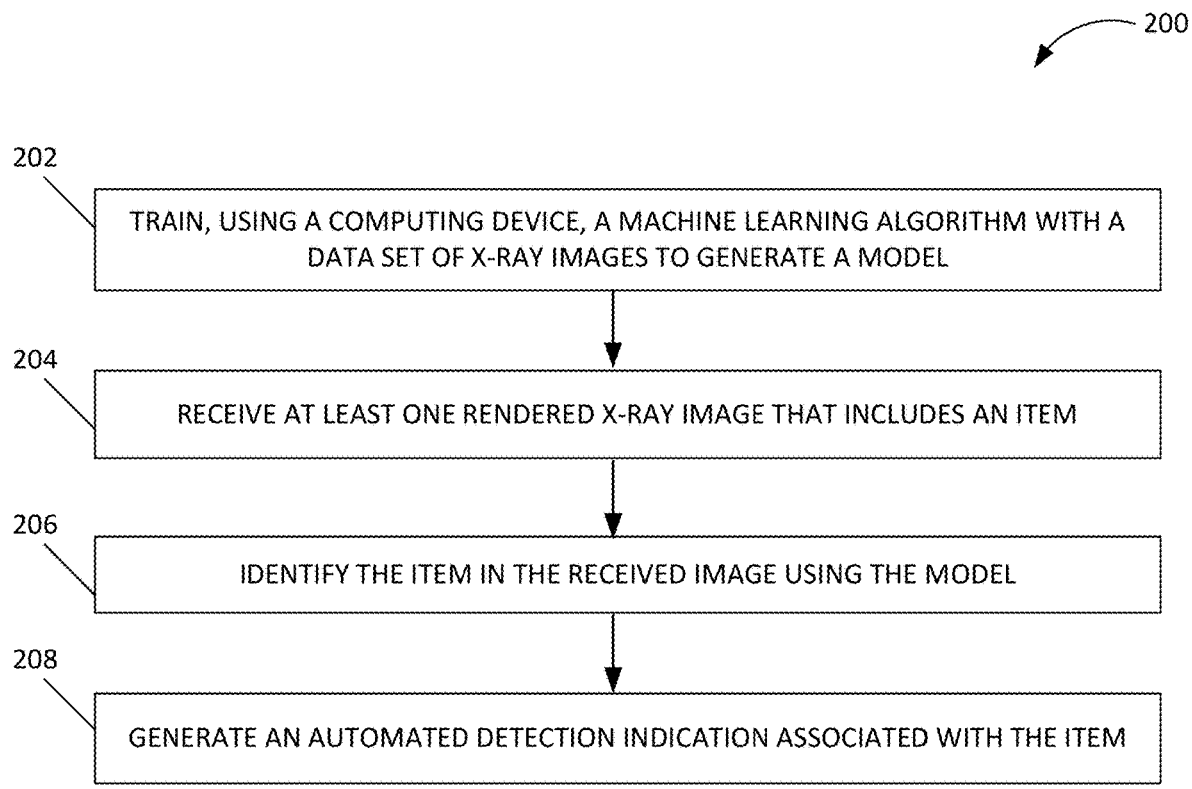
FIG. 2 is a flowchart illustrating an exemplary method employed by the image processing system, according to an example embodiment.

FIG. 2 is a flowchart illustrating an exemplary method 200 employed by the image processing system, according to an example embodiment. The method 200 may be performed using or one or more modules of system 100 described above.

At block 202, the machine learning algorithm employed in the image processing system 100 is trained for analyzing a specific format or type of image using a training data set. The machine learning algorithm module 110 may be configured to execute the machine learning algorithm. The training data module 120 may be configured to provide the training data set to the machine learning algorithm module 110 for training.

In an example embodiment, the training data set includes multiple x-ray images of items, luggage and packages. In an example embodiment, the training data set includes a first set of x-ray images of items containing a threat and a second set of x-ray images of items not containing a threat. This training data set can be used to train the machine learning algorithm determine whether an x-ray image of an item contains a threat or does not contain a threat. In another embodiment, the training data set includes a first set of x-ray images containing a specified item (e.g., a personal electronic device, a laptop, a container, a shoe, etc.) and a second set of x-ray images not containing the specified item. This training data set can be used to train the machine learning algorithm to identify a specified item in an x-ray image.

In an example embodiment, the machine learning algorithm is trained using a training data set that is based on the results or outputs of an existing explosive detection system. The existing explosive detection system may automatically determine if an input x-ray image includes an explosive or other weapon items. The results or outputs of the existing explosive detection system may include output images with indications that the image includes an explosive or other weapon items.

In an example embodiment, the images in the training data set are manually identified or labeled as including a specified item or not including a specified item. In an alternative embodiment, the images in the training data are automatically identified or labeled, using an automated system, as including a specified item or not including a specified item. An automated labeling system can perform the same function as a human in annotating or classifying the training data.

The images may be TRI-MAT images obtained via x-ray screening machines or devices, where the TRI-MAT images identify items in the images as organic, inorganic, or metallic objects. Each type of object is depicted as a different color in the TRI-MAT image. In a non-limiting example, the images for the training data set are obtained from a scanning device installed at a security checkpoint in a facility, such as an airport, a bus terminal, a train station, a government facility, a port or border control, a secure commercial facility, and the like.

In an example embodiment, the training data set may include 2D images. In another example, the training data set may include multiple 2D images representing different layers of an object. The 2D images may be cross-sectional images or slices of an object. In yet another example, the training data set may include multiple images each representing a different perspective of an object.

In an example embodiment, the training data set includes images to train the machine learning algorithm to analyze x-ray images and identify the presence of a specified object. The specified object may be, for example, an electronic device, a mobile computing device, a personal computing device, a laptop, a tablet, a smartphone, a cellular phone, a smartwatch, a bottle, container, a particular type of container (e.g., aerosol, liquid container, solid container, etc.) a shoe or pair of shoes, weapons, guns, or knives. The specified object may be an item or object that may be used to house an explosive device. In an example embodiment, the training data set includes images to train the machine learning algorithm to analyze x-ray images and identify the presence of a threat (e.g., explosive device). To train the machine learning algorithm for this objective, the training data set may include a first training data set that includes images depicting the items, luggage or packages that include the specified object. The training data set may include a second training data set that includes images depicting items, luggage or packages that do not include the specified object. The training data set may include a third training data set that includes images depicting items, luggage or packages that include a threat (e.g., explosive device). The training data set may include a fourth training data set that includes images depicting items, luggage or packages that include the specified object and a threat included in the specified object.

In an example embodiment, the machine learning algorithm employed by the image processing system 100 is a deep learning CNN. In machine learning, a convolutional neural network (CNN) is a type of feed-forward artificial neural network in which the connectivity pattern between its neurons is inspired by the organization of the animal visual cortex. Individual cortical neurons respond to stimuli in a restricted region of space known as the receptive field. The receptive fields of different neurons partially overlap such that they tile the visual field. The response of an individual neuron to stimuli within its receptive field can be approximated mathematically by a convolution operation.

In an example implementation, the algorithm architecture for a deep learning CNN employed by the image processing system 100 is an algorithm architecture provided or developed by Google Inc. and is called Google Inception™. In an example embodiment, the deep learning CNN algorithm architecture is AlexNet™ or GoogLeNet™.

In an example embodiment, an artificial neural network is trained by showing it millions of training examples and gradually adjusting the network parameters until it provides the desired classifications. The network, in one example, consists of 10 to 30 stacked layers of artificial neurons. Each image is fed into the input layer, which then communicates to the next layer, until eventually the "output" layer is reached. The network's "answer" or analysis is provided by this final output layer.

Each layer of the neural network progressively extracts higher and higher-level features of the image, until the final layer makes a decision on what the image shows. For example, the first layer may identify edges or corners. Intermediate layers may interpret the basic features to look for overall shapes or components, like a door or a leaf. The final few layers assemble those into complete interpretations.

In an example embodiment, the machine learning algorithm is trained and executed using a suitable framework or platform. In an example implementation, the Google Inception algorithm architecture is executed using the Caffe framework provided by University of California, Berkeley. The anatomy of the Caffe framework includes nets, layers, and blobs. The Caffe framework includes forward and backward computations of the layered compositional models. The task that has to be learned by the Caffe framework is referred to as "loss." The Caffe framework also includes the solver to coordinate model optimization.

Deep networks are compositional models that are naturally represented as a collection of inter-connected layers that work on chunks of data. The Caffe framework defines a net layer-by-layer in its own model schema. The network defines the entire model bottom-to-top from input data to loss. As data and derivatives flow through the network in the forward and backward passes, Caffe stores, communicates, and manipulates the information as blobs. A blob, as used with respect to Caffe, is a standard array and unified memory interface for the framework. The layer comes next as the foundation of both model and computation. The net follows as the collection and connection of layers. The details of blob describe how information is stored and communicated in and across layers and nets.

A blob, as used herein, is a wrapper over the actual data being processed and passed along by Caffe, and also under the hood provides synchronization capability between the CPU and the GPU. Mathematically, a blob is an N-dimensional array stored in a C-contiguous fashion. Caffe stores and communicates data using blobs. Blobs provide a unified memory interface holding data; e.g., batches of images, model parameters, and derivatives for optimization. Blobs conceal the computational and mental overhead of mixed CPU/GPU operation by synchronizing from the CPU host to the GPU device as needed. Memory on the host and device is allocated on demand (lazily) for efficient memory usage.

The conventional blob dimensions for batches of image data are number N×channel K×height H×width W. Blob memory is row-major in layout, so the last/rightmost dimension changes fastest. For example, in a 4D blob, the value at index (n, k, h, w) is physically located at index ((n*K+k)*H+h)*W+w, where number/N is the batch size of the data. Batch processing achieves better throughput for communication and device processing. For a training batch of 256 images N=256. Channel/K is the feature dimension, e.g., for RGB images K=3.

Parameter blob dimensions vary according to the type and configuration of the layer. For a convolution layer with 96 filters of 11×11 spatial dimension and 3 inputs the blob is 96×3×11×11. For an inner product/fully-connected layer with 1000 output channels and 1024 input channels the parameter blob is 1000×1024.

A blob synchronizes values between the CPU and GPU in order to hide the synchronization details and to minimize data transfer. In practice when GPUs are present, one loads data from the disk to a blob in CPU code, calls a device kernel to do GPU computation, and ferries the blob off to the next layer, ignoring low-level details while maintaining a high level of performance. As long as all layers have GPU implementations, all the intermediate data and gradients will remain in the GPU.

The layer is the essence of a model and the fundamental unit of computation. Layers convolve filters, pool, take inner products, apply nonlinearities like rectified-linear and sigmoid and other elementwise transformations, normalize, load data, and compute losses like softmax and hinge.

A layer takes input through bottom connections and makes output through top connections. Each layer type defines three critical computations: setup, forward, and backward. During setup, Caffe initializes the layer and its connections once at model initialization. During forward, Caffe given input from bottom computes the output and send to the top. During backward, Caffe given the gradient with respect to the top output computes the gradient with respect to the input and sends to the bottom. A layer with parameters computes the gradient with respect to its parameters and stores it internally.

More specifically, there are two Forward and Backward functions implemented, one for CPU and one for GPU. If a GPU version is not implemented, the layer falls back to the CPU functions as a backup option. This is useful for quick experiments, although it may come with additional data transfer cost (its inputs will be copied from GPU to CPU, and its outputs are copied back from CPU to GPU).

Layers have two key responsibilities for the operation of the network as a whole: a forward pass that takes the inputs and produces the outputs, and a backward pass that takes the gradient with respect to the output, and computes the gradients with respect to the parameters and to the inputs, which are in turn back-propagated to earlier layers. These passes are simply the composition of each layer's forward and backward.

Developing custom layers requires minimal effort by the compositionality of the network and modularity of the code. Define the setup, forward, and backward for the layer and it is ready for inclusion in a net.

The net jointly defines a function and its gradient by composition and auto-differentiation. The composition of every layer's output computes the function to do a given task, and the composition of every layer's backward computes the gradient from the loss to learn the task. Caffe models are end-to-end machine learning engines. The net is a set of layers connected in a computation graph—a directed acyclic graph (DAG) to be exact. Caffe does all the bookkeeping for any DAG of layers to ensure correctness of the forward and backward passes. A typical net begins with a data layer that loads from disk and ends with a loss layer that computes the objective for a task such as classification or reconstruction.

The net is defined as a set of layers and their connections in a plaintext modeling language. The construction of the network is device agnostic—blobs and layers hide implementation details from the model definition. After construction, the network is run on either CPU or GPU. Layers come with corresponding CPU and GPU routines that produce identical results (up to numerical errors).

The models are defined in plaintext protocol buffer schema (prototxt) while the learned models are serialized as binary protocol buffer (binaryproto) .caffemodel files.

Caffe speaks Google Protocol Buffer for the following strengths: minimal-size binary strings when serialized, efficient serialization, a human-readable text format compatible with the binary version, and efficient interface implementations in multiple languages, most notably C++ and Python. This all contributes to the flexibility and extensibility of modeling in Caffe.

The forward and backward passes are the computations of a Net. The forward pass computes the output given the input for inference. In forward Caffe composes the computation of each layer to compute the "function" represented by the model. This pass goes from bottom to top. The backward pass computes the gradient given the loss for learning. In backward Caffe reverse-composes the gradient of each layer to compute the gradient of the whole model by automatic differentiation. This is back-propagation. This pass goes from top to bottom.

The backward pass begins with the loss and computes the gradient with respect to the output. The gradient with respect to the rest of the model is computed layer-by-layer through the chain rule. Layers with parameters compute the gradient with respect to their parameters during the backward step. These computations follow immediately from defining the model. Caffe plans and carries out the forward and backward passes.

The Solver optimizes a model by first calling forward to yield the output and loss, then calling backward to generate the gradient of the model, and then incorporating the gradient into a weight update that attempts to minimize the loss. Division of labor between the Solver, Net, and Layer keep Caffe modular and open to development.

Solving is configured separately to decouple modeling and optimization. The solver orchestrates model optimization by coordinating the network's forward inference and backward gradients to form parameter updates that attempt to improve the loss. The responsibilities of learning are divided between the Solver for overseeing the optimization and generating parameter updates and the Net for yielding loss and gradients.

In Caffe, learning is driven by a loss function (also known as an error, cost, or objective function). A loss function specifies the goal of learning by mapping parameter settings (i.e., the current network weights) to a scalar value specifying the "badness" of these parameter settings. Hence, the goal of learning is to find a setting of the weights that minimizes the loss function.

The loss in Caffe is computed by the Forward pass of the network. Each layer takes a set of input (bottom) blobs and produces a set of output (top) blobs. In one embodiment, some of these layers' outputs may be used in the loss function.

To create a Caffe model, the model architecture is defined in a protocol buffer definition file (prototxt). Data enters Caffe through data layers: they lie at the bottom of nets. Data can come from efficient databases (LevelDB or LMDB), directly from memory, or, when efficiency is not critical, from files on disk in HDF5 or common image formats.

There are four steps in training a CNN using Caffe. The first step includes data preparation. In this step, the images are cleaned and stored in a format that can be used by Caffe. In an example embodiment, a Python script executed by the input data module 130 may handle image pre-processing and storage, selection of suitable images for a training set, and application of any preprocessing steps, such as colorization.

The second step includes model definition. In this step, a CNN architecture is chosen, its parameters are defined in a configuration file. For example, the CNN architecture chosen for the image processing system described herein may be Google Inception version 1. One schooled in the art will understand that many multilayer CNN model architectures are available and enable the performance of the detection task.

In the third step, the solver parameters are defined in a configuration file. The solver is responsible for model optimization.

In the fourth step, the model is trained using the training data set described herein. After training the model, Caffe generates the trained model in a file.

After the training phase, the generated trained models can be used to identify the presence of a specified object within an input image, and, if the specified object exists in the image, determine if the specified object includes a threat.

In other embodiments, other machine learning frameworks may be used to implement the deep learning CNN algorithm. Other frameworks may include Torch™, Theano™, and TensorFlow™.

Figure 3:
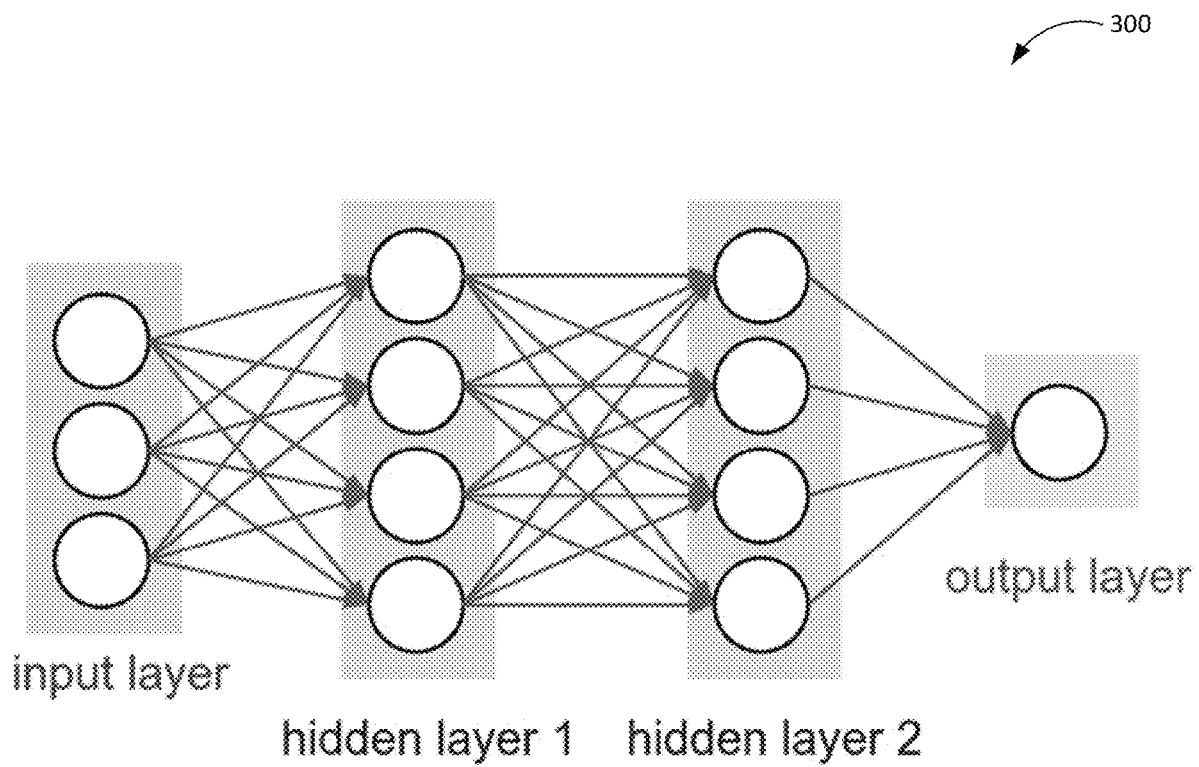
FIG. 3 illustrates an exemplary convolutional neural network employed by the image processing system, according to an example embodiment.

The image processing system 100 stores the one or more models generated by the trained machine learning algorithm. In an example embodiment, models generated by the deep learning CNN consists of an input layer, at least two hidden layers, and an output layer as depicted in FIG. 3. As described above, a machine-learned model includes machine-learned weights, coefficients, and forms that are inherent in training a CNN algorithm.

Continuing with the discussion of FIG. 2, at block 204, the input data module 130 receives at least one rendered x-ray image that includes an item. In a non-limiting example, the input x-ray image is obtained from a scanning device installed at a security checkpoint in a facility, such as an airport, a bus terminal, a train station, a government facility, a port or border control, a secure commercial facility and the like.

The image processing system 100 executes one or more machine-learned models generated by training the machine learning algorithm using the training data set to analyze the input image and identify presence of a specified object.

At block 206, the machine learning algorithm module 110 is configured to, using the generated models, analyze the input image received at block 204, and automatically determine if the input image includes a specified object. After determining that the specified object is present or included in the image, the image processing device, in an example embodiment, determines whether the specified object includes a threat. For example, the image processing system 100 determines that the image includes a laptop (specified object). Then the image processing system 100 determines whether the laptop includes a threat, for example, an explosive device.

At block 208, the output data module 140 generates an automated detection indication associated with the item identified in the input image. In an example embodiment, the automated detection indication is a text label or other graphical indication that identifies a specified item in the input image. The automated detection indication may be displayed on or included in an output image provided at a display of a user device. The output image may be the input image (e.g., a rendered x-ray image) with an indication of the presence of a specified item. As described herein, the user device where the output or the automated detection indication is provided to the user may include a display device coupled to security scanning device, a computing device, or a server. In another embodiment, the automated detection indication may be a visual indication indicating the location of the specified item in the input image. Such visual indication may be a colored box shape enclosing the specified item. In another embodiment, the automated detection indication may be a graphical indication and/or an audible indication alerting a user that an item containing a threat is detected in the input image.

The automated detection indication is based at least in part on machine-learned features of the item in the input image, where the machined-learned features of the item are based on the training data set of x-ray images.

The automated detection indication may be transmitted to a user device or a computing device coupled to a security scanning device in a facility. In some embodiments, the security scanning device may be an x-ray screening machine in an airport or other secure facility. The automated detection indication may be generated and transmitted in real-time or near real-time with respect to when the input image is received at the image processing system 100.

The machine learning algorithm employed in the image processing system requires time for training and set up. After training, the machine learning algorithm is able to analyze an input image and generate an output in real-time or near real-time. Once trained, the image processing system may be used as a pre-screening system at security checkpoints. In one embodiment, a first abbreviated portion of the machine learning algorithm may be used to perform pre-screening. In some embodiments, the output of the image processing system may be an alert that the luggage corresponding to the image requires further processing. In an embodiment, following the generation of the alert, a second more time intensive portion of the machine learning algorithm may be executed on the image or luggage. In contrast, if the initial pre-screening generates an all-clear indication, then the luggage may not be further analyzed. Thus, the image processing system described herein may be employed to increase efficiency in image processing and speed up the security scanning process at a facility.

In an example embodiment, the image processing system 100 determines that the identified item at block 206 is a common false-alarm object for explosive detection systems. In an example embodiment, a list of common false-alarm objects is stored in a database. False-alarm objects identified by the image processing system are dependent on the machine learning algorithm employed by the system. In an example embodiment, objects that may be identified by the image processing system but are common false-alarms objects in terms of threat or explosives may be aggregated to generate a list of common false-alarm objects to enable a particular machine learning algorithm to account for the false alarm objects.

Figure 4B:
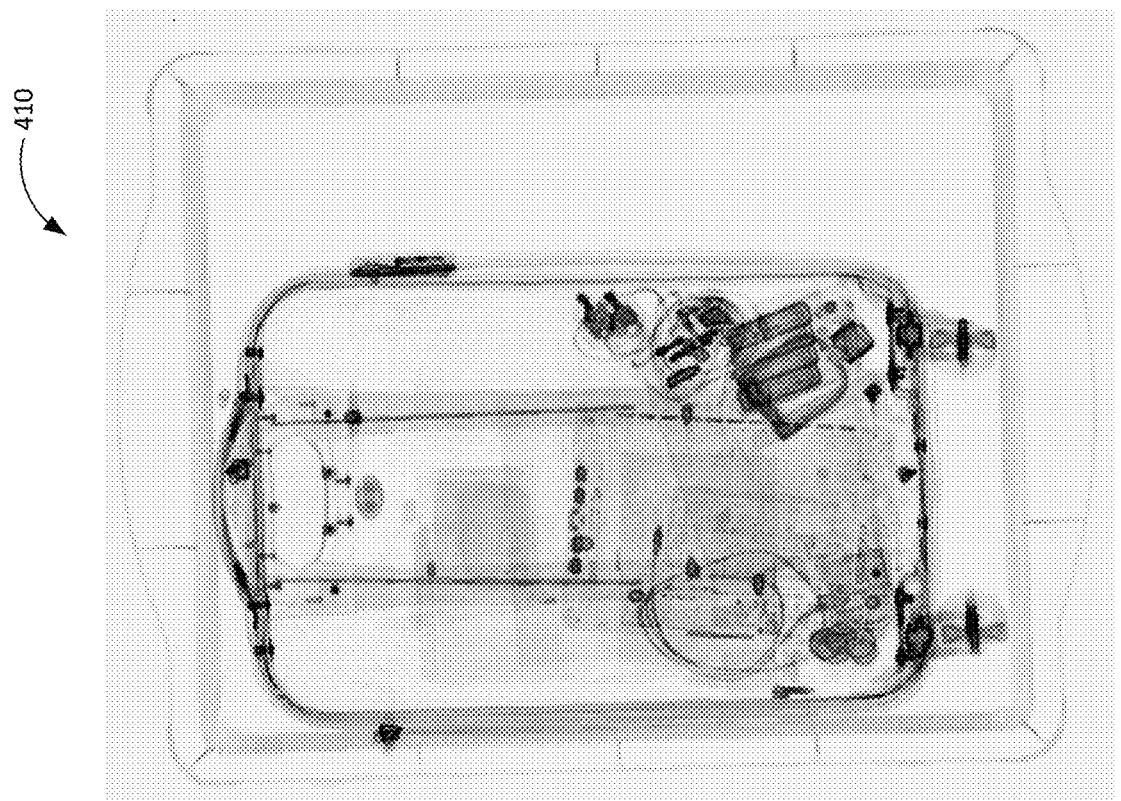
FIG. 4B shows an output image provided by the image processing system, according to an example embodiment.
Figure 4A:
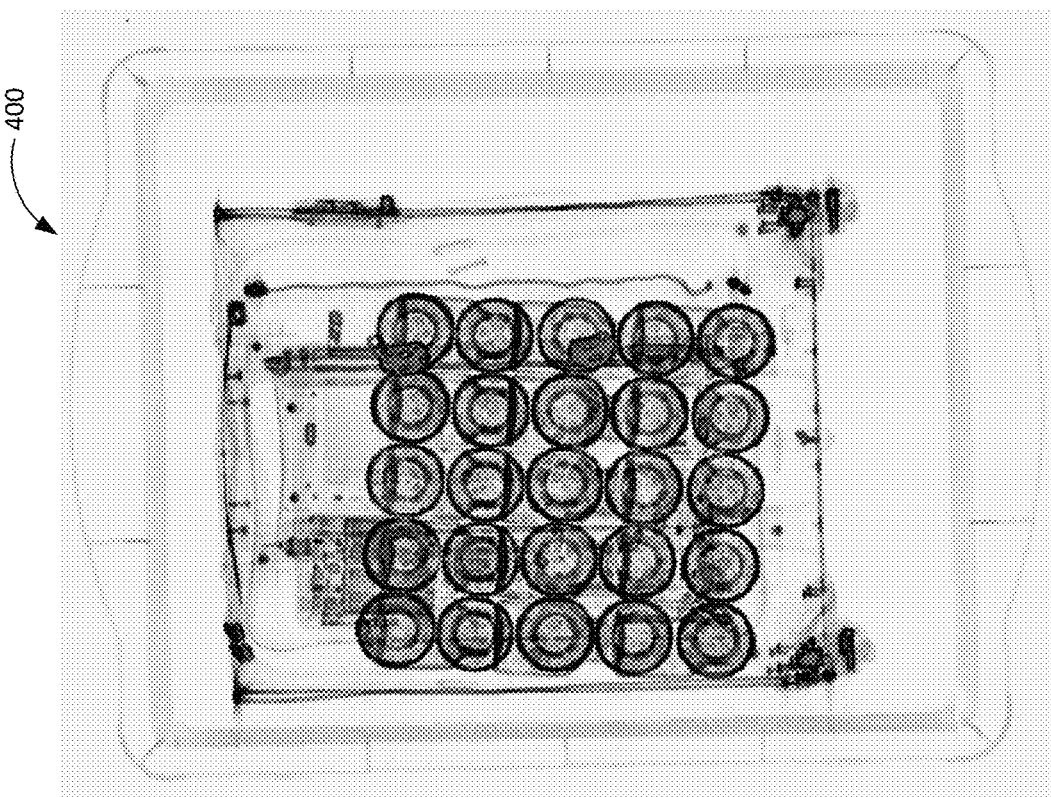
FIG. 4A shows an output image provided by the image processing system, according to an example embodiment.

FIGS. 4A and 4B show output images 400 and 410 respectively provided by the image processing system described herein. The output images 400 and 410 illustrate that the image processing system successfully identified the presence of a specified object, in this case a laptop, within the image.

Figure 4D:
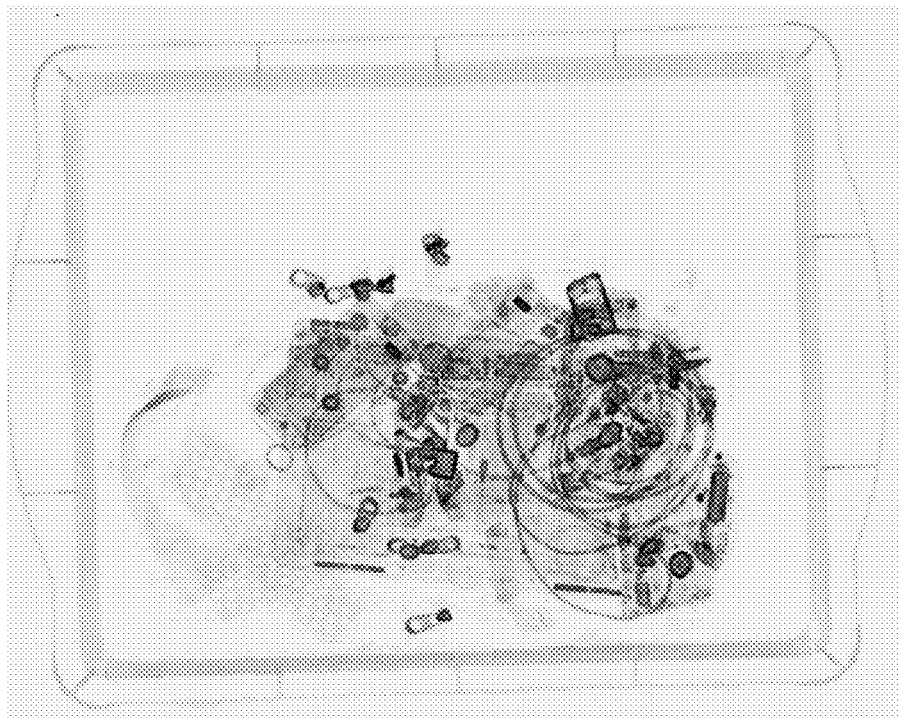
FIG. 4D shows an output image provided by the image processing system, according to an example embodiment.
Figure 4C:
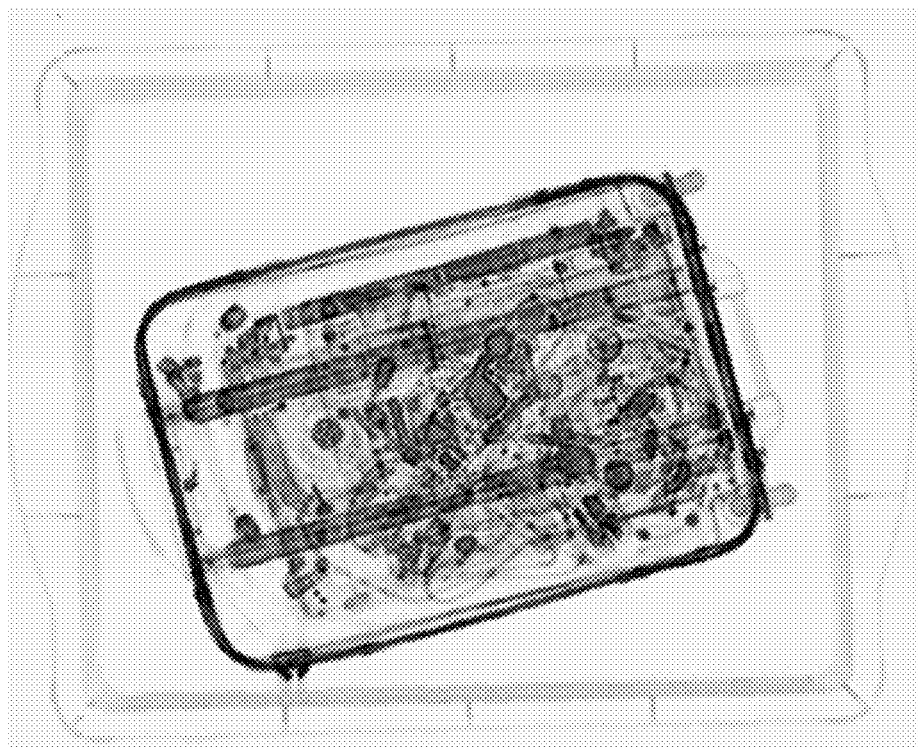
FIG. 4C shows an output image provided by the image processing system, according to an example embodiment.

FIGS. 4C and 4D show output images 400 and 410 respectively provided by the image processing system described herein. The output images 420 and 430 illustrate that the image processing system successfully identified the presence of a specified object, in this case a laptop, within the image.

Figure 5B:
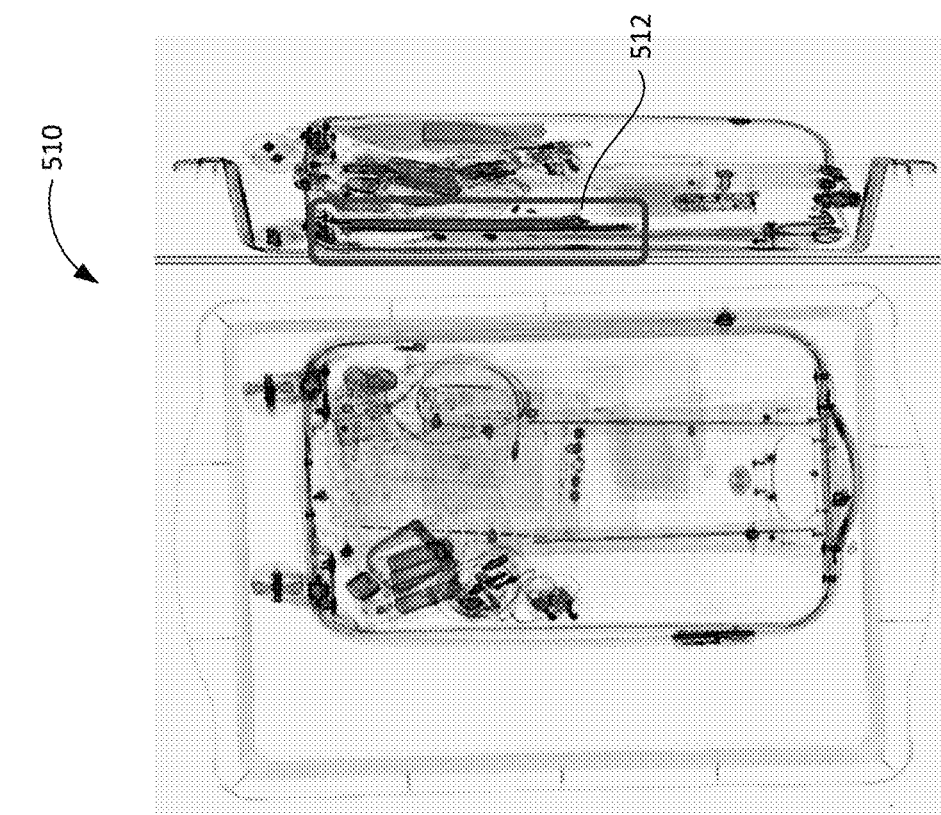
FIG. 5B shows an output image provided by the image processing system, according to an example embodiment.
Figure 5A:
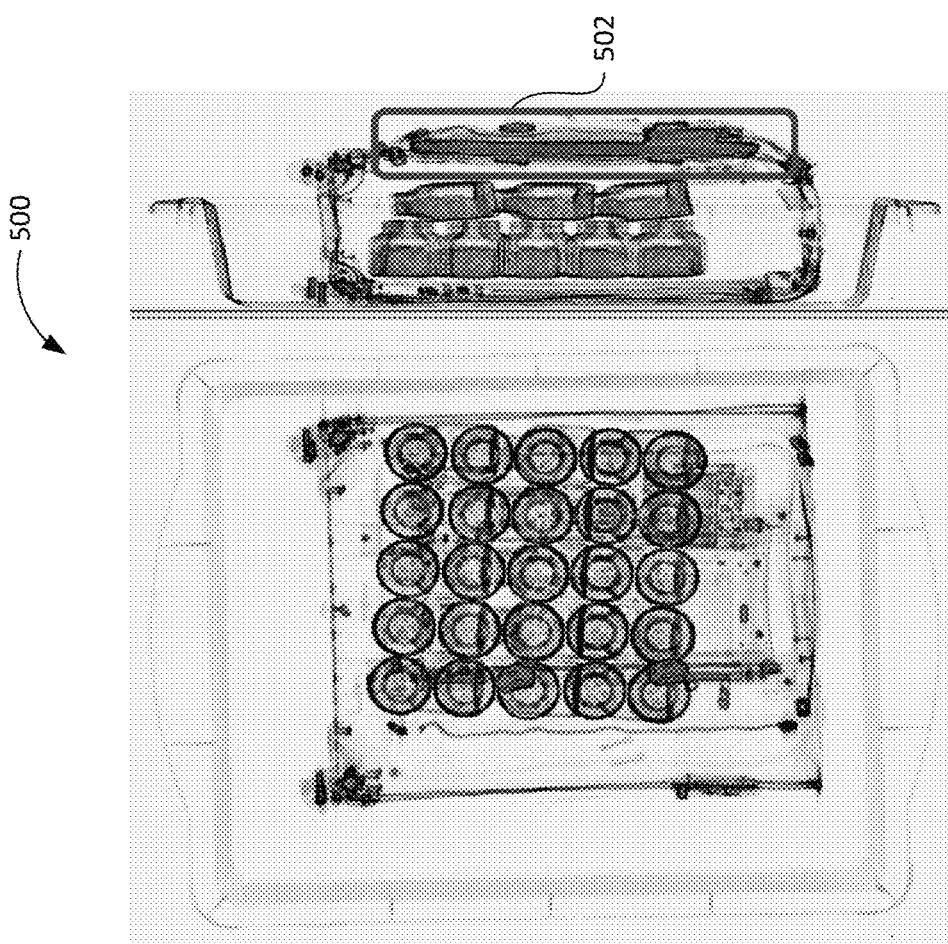
FIG. 5A shows an output image provided by the image processing system, according to an example embodiment.

FIG. 5A shows an output image 500 of the image processing system 100. The output image 500 includes a front perspective view and a side perspective view of the luggage depicted in the image of FIG. 4A. FIG. 5B shows an output image 510 of the image processing system 100. The output image 510 includes a front perspective view and a side perspective view of the luggage depicted in the image of FIG. 4B. As described herein, the output images are based on the input images and include an automated detection indication. As shown in images 500 and 510, the location of a specified item (e.g., laptop) is shown using a colored shape 502 and 512 respectively. In example embodiments, the input rendered x-ray images include perspective views of the item, luggage or package scanned for security purposes.

Figure 6:
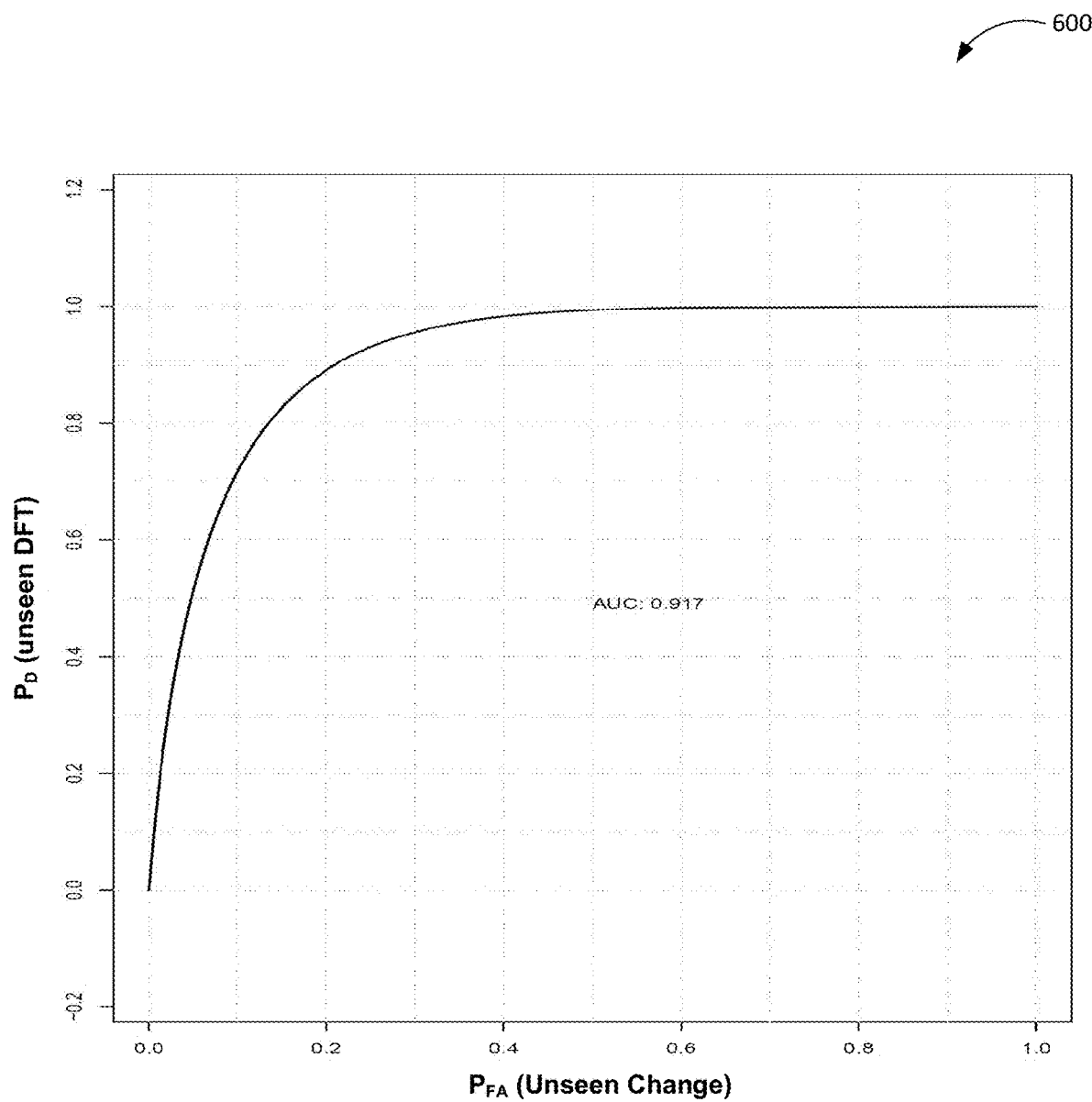
FIG. 6 is a graph illustrating a false positives and true positives error rate of the image processing system, according to an example embodiment.

Testing of an exemplary trained machine learning algorithm employed by the image processing system described herein, presented a 95.6% probability of detection (PD) of threats in images. In an additional application identifying a specific type of threat, based on the results of testing the system, the graph 600 (Relative Operating Characteristic) illustrated in FIG. 6 is provided. As shown in the graph, the x-axis shows the probability of a false alarm (PFA), and the y-axis shows the PD. The area under the curve (AUC) is calculated to be 0.917.

In this manner, the image processing system described herein enables analysis of images and automatic identification of specified items and threats. The image processing system employs a machine learning algorithm, such as deep learning CNN, to analyze the images. Past attempts by others to train a deep learning CNN algorithm to analyze x-ray images to detect threats in items, luggage and packages were unsuccessful because the size of the training data set needed to train such a machine learning algorithm was unknown. Conventionally it was assumed that the training data set had to be very large, and that such a large data set for training the machine learning algorithm was unobtainable. However, embodiments of the image processing system described herein may be trained with a smaller training data set (e.g., approximately 5,000 to 10,000 images may be used to train a deep learning CNN algorithm) to analyze x-ray images to identify specified objects and threats in items, luggage and packages. Additionally, as described herein, embodiments use a specific type of training data set to train a deep learning CNN algorithm to analyze x-ray images to identify specified objects and threats in items, luggage and packages.

Conventionally, one skilled in the art has been able to use existing deep learning CNN algorithms to analyze optical images or 2D images. However, attempts to use existing deep learning CNN algorithms to analyze x-ray images or colorized x-ray images result in an output that is nonsensical. In contrast, embodiments of the present invention retrain a deep learning CNN algorithm using a training data set consisting of x-ray images or colorized x-ray images to enable the image processing system described herein to perform the functionalities described herein that result in an accurate analysis of x-ray images and/or colorized x-ray images.

Conventionally, one skilled in the art may employ a trained deep learning CNN algorithm to perform analysis on his or her input data and may retrain a deep learning CNN algorithm to perform his or her desired analysis. Conventionally this retraining has been done by retraining only a certain percentage of layers, for example 50-80% of the layers, based on the transferred learning technique for CNN. However, in some embodiments of the present invention, in, 100% of the layers of the deep learning CNN algorithm are retrained to be able to analyze x-ray images or colorized x-ray images to identify a specified object and threat. In one embodiment, greater than 95% of the layers of the layers of the deep learning CNN algorithm are retrained to be able to analyze x-ray images or colorized x-ray images to identify a specified object and threat.

The use of a deep multi-layer CNN approach traditionally requires large amounts of training data in order to facilitate construction of a complex complete end-to-end feature extraction, representation, and classification process. Modern CNN approach typically include varying number of layers (3-22) within their structure. Presently, such CNNs are designed manually with the resulting parametrization of the networks performing training using a stochastic gradient descent approach with varying parameters such as batch size, weight decay, momentum and learning rate over a huge data set (typically $10^6$ in size). However, the limited applicability of such training and parameter optimization techniques to problems where such large datasets are not available gives rise to the concept of transfer learning.

Within the context of x-ray security screening, limited availability of training for particular items of interest can thus pose a problem. To overcome this issue, embodiments employ a transfer learning paradigm such that a pre-trained CNN, primarily trained for generalized image classification tasks where sufficient training data exists, can be specifically optimized as a later secondary process that targets a specific application domain. Each hidden layer in a CNN has distinct feature representation related characteristics among which the lower layers provide general features extraction capabilities, whilst higher layers carry information that is increasingly more specific to the original classification task. This finding facilitates the verbatim re-use of the generalized feature extraction and representation of the lower layers in a CNN, whilst higher layers are fine-tuned towards secondary problem domains with related characteristics to the original. Using this paradigm, embodiments leverage the priori CNN parametrization of an existing fully trained network, on a generic 1000+ object class problem, as a starting point for optimization towards the specific problem domain of limited object class detection within x-ray images. Instead of designing a new CNN with random parameter initialization, embodiments adopt a pretrained CNN and fine tune its parameterization towards a specific classification domain. One embodiment uses Google Inception version 1 with 6 million parameters. In an embodiment, zero or more layers may not be retrained.

FIG. 7 schematically depicts an exemplary system for training the CNN. As described herein, training of the CNN algorithm starts with a sequence of layers 710, a set of initialized parameters 720 and a set of training data 730. In an example embodiment, the training data 730 is stored as folders of multiple images, where each folder corresponds to one class of data. That is, a first folder may contain images with laptops, a second folder may contain images without laptops, a third folder may contain images with bottles, a fourth folder may contain images without bottles, and so on. During training, each layer's parameters 720 may be updated or frozen as indicated by the lock icons 715. After training, the CNN model with the updated parameters and the sequence of layers is used to analyze input images to identify specified items and threats therewithin.

Some conventional systems, freeze certain layers of a pre-trained CNN algorithm to use certain existing machine-learned features of the pre-trained CNN. In an example embodiment, the systems and methods described herein retrain all the layers of an existing CNN algorithm to enable the CNN algorithm to generate new machine-learned features, weights and coefficients based on the training data set. Some conventional systems also train a machine learning algorithm on particular portions or sections of an image that contain a specified item. However, the systems and methods described herein train the machine learning algorithm on whole or entire images that contain specified items, rather than isolating a portion of the image that contains the item. In an example embodiment, the image processing system described herein is trained on multiple views or dimensions of an image, as illustrated in FIGS. 5A and 5B. In an example embodiment, the image processing system described herein is trained using the same number of images for a particular class of items. That is, the training data set includes the same number of images that have a specified item and the same number of images that do not have the specified item. Similarly, the training data set includes the same number of images that include an item containing a threat and the same number of images that include an item without a threat. In contrast, conventional systems use training data sets that have an unequal number of images for particular classes of items.

To implement the image processing system described herein, an exemplary embodiment employs a computing device running LINUX, one or more graphics processing cards or units (GPUs), thousands of images for training, and a deep learning CNN framework (e.g., Caffe).

Appendix A submitted with the present disclosure illustrates steps of an example CNN algorithm trained according to the present disclosure to analyze an example x-ray input image that includes a container (e.g., bottle). The example CNN of Appendix A is generated by training a Google Inception™ CNN algorithm. Appendix A illustrates an exemplary network architecture and the output of the network at each stage for the machine learning algorithm employed by the image processing system described herein.

Appendix B submitted with the present disclosure illustrates steps of an example CNN algorithm that is not trained according to the present disclosure, and rather is trained using conventional methods where certain layers of the CNN are frozen. As seen in Appendix B, the classification output which correctly indicated a bottle after training does not do so with the existing pre-trained machine learning algorithm.

Figure 8:
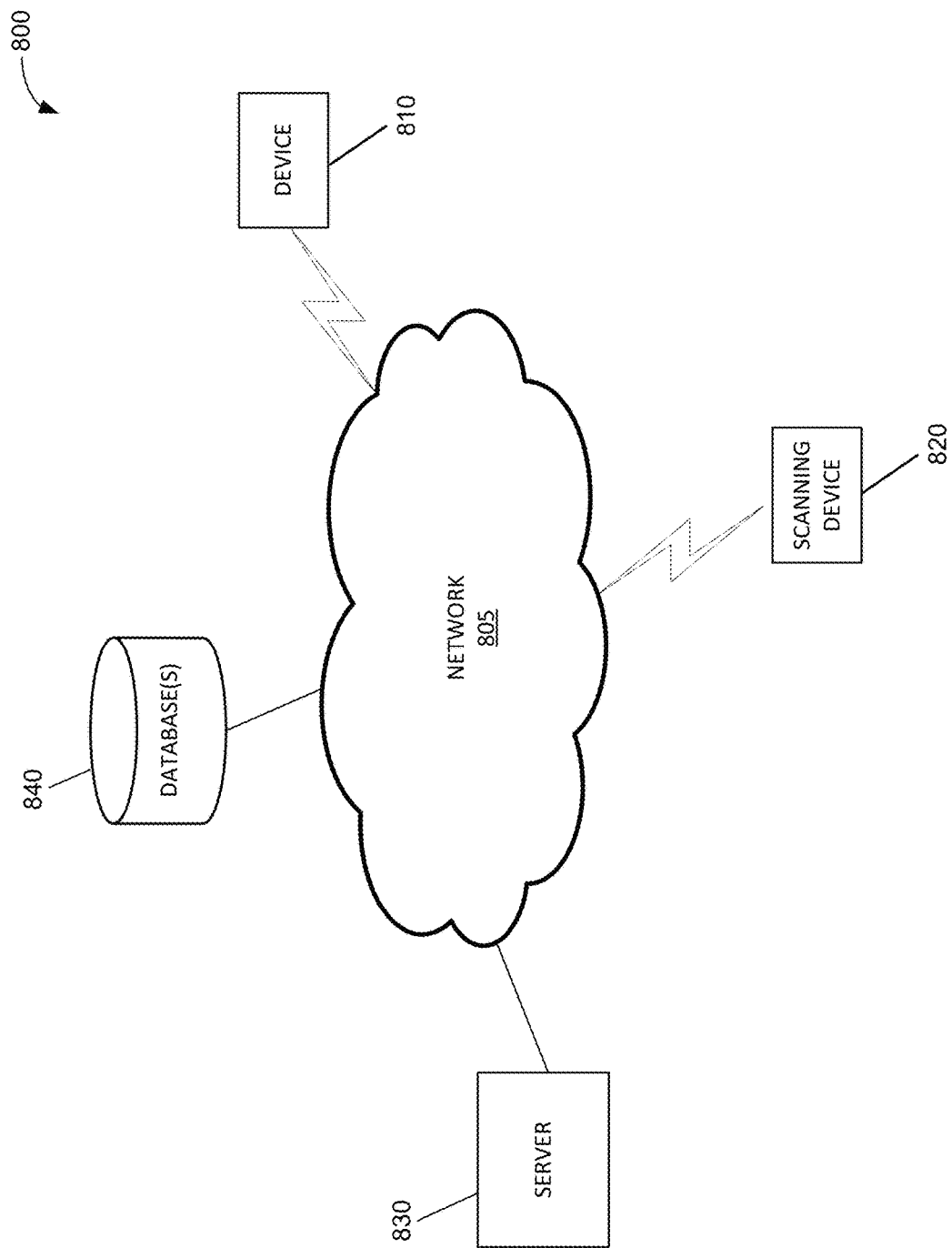
FIG. 8 illustrates a network diagram depicting a system for implementing the image processing system, according to an example embodiment.

FIG. 8 illustrates a network diagram depicting a system 800 for implementing the image processing system, according to an example embodiment. The system 800 can include a network 805, multiple devices, for example, device 810, scanning device 820, server 830, and a database(s) 840. Each of the devices 810, 820, server 830, and database(s) 840 is in communication with the network 805.

In an example embodiment, one or more portions of network 805 may be an ad hoc network, an intranet, an extranet, a virtual private network (VPN), a local area network (LAN), a wireless LAN (WLAN), a wide area network (WAN), a wireless wide area network (WWAN), a metropolitan area network (MAN), a portion of the Internet, a portion of the Public Switched Telephone Network (PSTN), a cellular telephone network, a wireless network, a WiFi network, a WiMax network, any other type of network, or a combination of two or more such networks.

The device 810 may include, but are not limited to, work stations, computers, general purpose computers, Internet appliances, hand-held devices, wireless devices, portable devices, wearable computers, cellular or mobile phones, portable digital assistants (PDAs), smart phones, tablets, ultrabooks, netbooks, laptops, desktops, multi-processor systems, microprocessor-based or programmable consumer electronics, network PCs, mini-computers, and the like. Device 810 may connect to network 805 via a wired or wireless connection.

The scanning device 820 may include an x-ray machine or system to scan items, such as luggage, packages, containers, and other items, and produce rendered x-ray images of scanned items on a display device coupled to the scanning device 820. In an example embodiment, the scanning device 820 is a security screening system at a checkpoint at an airport. The scanning device 820 may be used to scan passengers' luggage and carry-on items for security purposes. In an example embodiment, the images produced by the scanning device 820 are used as the dataset to train the machine learning algorithm as described herein. In other embodiments, the scanning device 820 produces the input image for the image processing system 100. After the input image is processed, the output image may be displayed at the display device coupled to the scanning device 820, where the output image may include a label for the identified item, an indication of the location of the item within the image, and an indication of a threat status of the item. In an example embodiment, the scanning device 820 is a commercially available ClearScan® device.

As an add-on module, the image processing system described herein can be loaded as a software module onto an existing security checkpoint device or existing server networked to one or more devices. The image processing system generates an alarm and alerts the operator of the security checkpoint device to detected threats, in addition to any other detection technology that may be installed on those devices or servers. In this way, the image processing system adds detection capability, without clearing items that would generate an alarm via other channels or programs implemented on those devices or servers.

While one schooled in the art can appreciate that the add-on capability may be added to any x-ray imaging device, in one embodiment it may be added to a ClearScan® checkpoint scanner that has previously passed a general detection requirement with a separate algorithm. In this way, the alerts generated by the image processing system add-on described herein may be displayed on the screen along with alarms generated by other detection software.

In an example embodiment, the devices 810, 820 may perform one or more of the functionalities of the image processing system 100 described herein. The device 810, 820 can include one or more components of computing device 800 of FIG. 8. The device 810, 820 may be used to train the machine learning algorithm, and then use the trained algorithm on input images to identify presence of a specified object and threat.

In an example embodiment, the image processing system 100 may be included on the server 830, and the server 830 performs one or more of the functionalities of the image processing system 100 described herein. In some embodiments, the devices 810, 820 may perform some of the functionalities, and the server 830 performs the other functionalities described herein.

Each of the database(s) 840, and server 830 is connected to the network 805 via a wired or wireless connection. Server 830 includes one or more computers or processors configured to communicate with devices 810, 820 via network 805. The server 830 can include one or more components of device 900 of FIG. 9. Server 830 hosts one or more applications or websites, including the image processing system described herein, accessed by devices 810, 820 and/or facilitates access to the content of database(s) 840. Database(s) 840 include one or more storage devices for storing data and/or instructions (or code) for use by server 830, and/or devices 810, 820. Database(s) 840 and server 830 may be located at one or more geographically distributed locations from each other or from devices 810, 820. Alternatively, database(s) 840 may be included within server 830.

Figure 9:
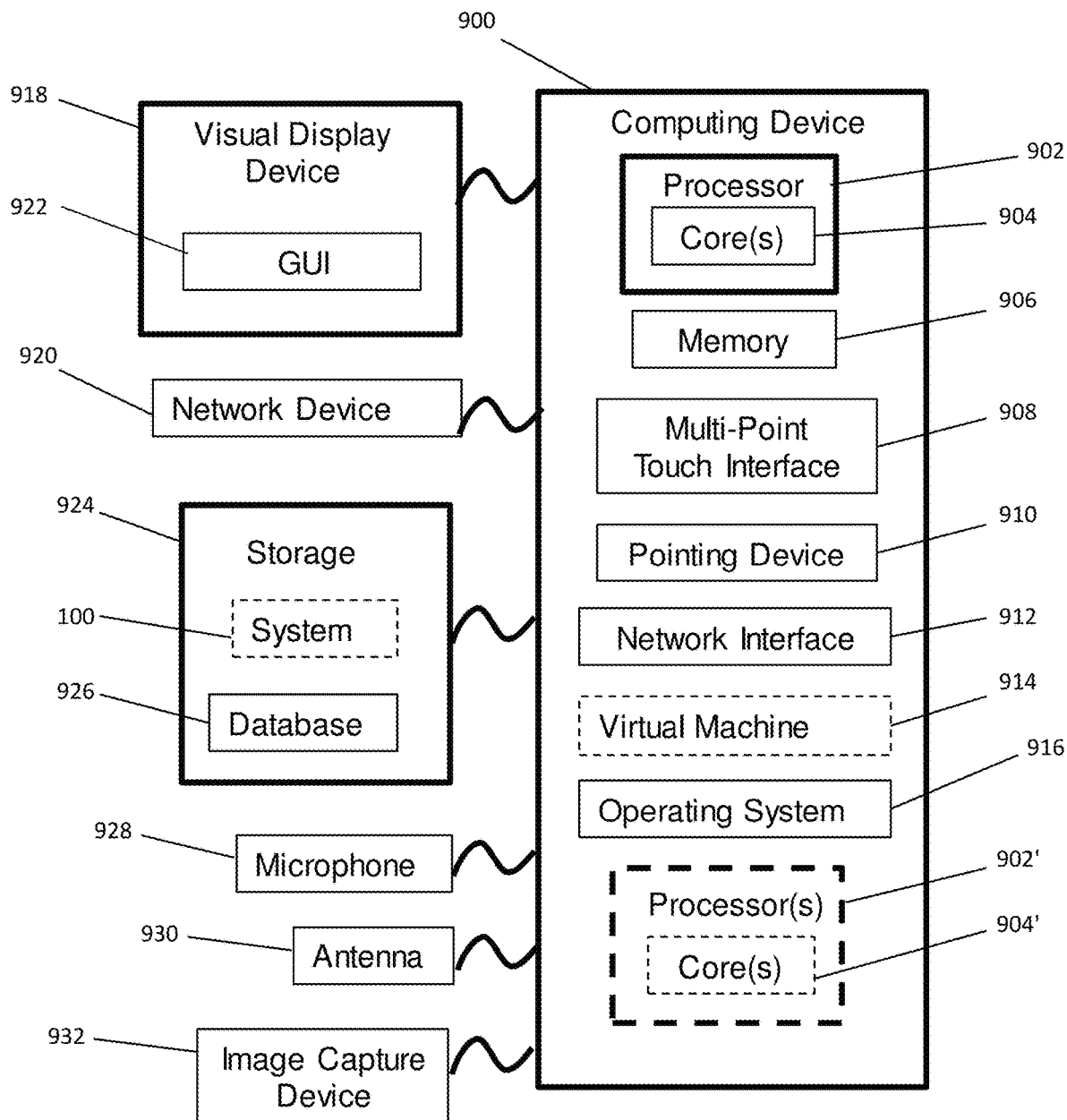
FIG. 9 is a block diagram of an exemplary computing device that can be used to perform one or more steps of the methods provided by exemplary embodiments.

FIG. 9 is a block diagram of an exemplary computing device 900 that can be used to perform one or more steps of the methods provided by exemplary embodiments. For example, computing device 900 may be, but is not limited to device 810, 820 and server 830 as described in FIG. 8. The computing device 900 includes one or more non-transitory computer-readable media for storing one or more computer-executable instructions or software for implementing exemplary embodiments. The non-transitory computer-readable media can include, but are not limited to, one or more types of hardware memory, non-transitory tangible media (for example, one or more magnetic storage disks, one or more optical disks, one or more USB flashdrives), and the like. For example, memory 906 included in the computing device 900 can store computer-readable and computer-executable instructions or software for implementing exemplary embodiments. The computing device 900 also includes processor 902 and associated core 904, and optionally, one or more additional processor(s) 902' and associated core(s) 904' (for example, in the case of computer systems having multiple processors/cores), for executing computer-readable and computer-executable instructions or software stored in the memory 906 and other programs for controlling system hardware. Processor 902 and processor(s) 902' can each be a single core processor or multiple core (904 and 904') processor. The computing device 900 also includes a graphics processing unit (GPU) 905. In some embodiments, the computing device 900 includes multiple GPUs.

Virtualization can be employed in the computing device 900 so that infrastructure and resources in the computing device can be shared dynamically. A virtual machine 914 can be provided to handle a process running on multiple processors so that the process appears to be using only one computing resource rather than multiple computing resources. Multiple virtual machines can also be used with one processor.

Memory 906 can include a computer system memory or random access memory, such as DRAM, SRAM, EDO RAM, and the like. Memory 906 can include other types of memory as well, or combinations thereof. A user can interact with the computing device 900 through a visual display device 918, such as a touch screen display or computer monitor, which can display one or more user interfaces 919. The visual display device 918 can also display other aspects, elements and/or information or data associated with exemplary embodiments. The computing device 900 can include other I/O devices for receiving input from a user, for example, a keyboard or any suitable multi-point touch interface 908, a pointing device 910 (e.g., a pen, stylus, mouse, or trackpad). The keyboard 908 and the pointing device 910 can be coupled to the visual display device 918. The computing device 900 can include other suitable conventional I/O peripherals.

The computing device 900 can also include one or more storage devices 924, such as a hard-drive, CD-ROM, or other computer readable media, for storing data and computer-readable instructions and/or software, such as one or more modules of the system 100 shown in FIG. 1 that implements exemplary embodiments of the notification system as described herein, or portions thereof, which can be executed to generate user interface 919 on display 918. Exemplary storage device 924 can also store one or more databases for storing any suitable information required to implement exemplary embodiments. The databases can be updated by a user or automatically at any suitable time to add, delete or update one or more items in the databases. Exemplary storage device 924 can store one or more databases 926 for storing provisioned data, and other data/information used to implement exemplary embodiments of the systems and methods described herein.

The computing device 900 can include a network interface 912 configured to interface via one or more network devices 922 with one or more networks, for example, Local Area Network (LAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, controller area network (CAN), or some combination of any or all of the above. The network interface 912 can include a built-in network adapter, network interface card, PCMCIA network card, card bus network adapter, wireless network adapter, USB network adapter, modem or any other device suitable for interfacing the computing device 900 to any type of network capable of communication and performing the operations described herein. Moreover, the computing device 900 can be any computer system, such as a workstation, desktop computer, server, laptop, handheld computer, tablet computer (e.g., the iPad® tablet computer), mobile computing or communication device (e.g., the iPhone® communication device), or other form of computing or telecommunications device that is capable of communication and that has sufficient processor power and memory capacity to perform the operations described herein.

The computing device 900 can run any operating system 916, such as any of the versions of the Microsoft® Windows® operating systems, the different releases of the Unix and Linux operating systems, any version of the MacOS® for Macintosh computers, any embedded operating system, any real-time operating system, any open source operating system, any proprietary operating system, any operating systems for mobile computing devices, or any other operating system capable of running on the computing device and performing the operations described herein. In exemplary embodiments, the operating system 916 can be run in native mode or emulated mode. In an exemplary embodiment, the operating system 916 can be run on one or more cloud machine instances.

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes multiple system elements, device components or method steps, those elements, components or steps may be replaced with a single element, component or step. Likewise, a single element, component or step may be replaced with multiple elements, components or steps that serve the same purpose. Moreover, while exemplary embodiments have been shown and described with references to particular embodiments thereof, those of ordinary skill in the art will understand that various substitutions and alterations in form and detail may be made therein without departing from the scope of the present disclosure. Further still, other embodiments, functions and advantages are also within the scope of the present disclosure.

What is claimed is:

1. A computing-device implemented method for identifying an item in an x-ray image using at least one computing device equipped with a processor, the method comprising:
   executing, using the at least one computing device, at least one machine-learned model, the at least one machine-learned model trained with at least one training data set of x-ray images, the at least one training data set including a first set of x-ray images of items containing threats and a second set of x-ray images of items not containing threats, and the first set of x-ray images or the second set of x-ray images include one or more volumetric x-ray images or one or more projection x-ray images;
   receiving, with the at least one computing device, at least one rendered x-ray image that includes an item, the x-ray image having a material information format that identifies items in the image as organic, inorganic or metallic;
   identifying, with the at least one computing device, the item using the at least one model; and
   generating, with the at least one computing device, an automated detection indication associated with the item.

2. The method of claim 1, wherein the at least one training data set includes a first set of x-ray images containing a specified item and second set of x-ray images not containing the specified item.

3. The method of claim 1, wherein the automated detection indication is based at least in part on machine-learned features of the item that are based on the at least one training data set.

4. The method of claim 1, wherein the machine-learned model includes weights, coefficients, and forms learned by analysis of the at least one training data set.

5. The method of claim 1, wherein the automated detection indication includes a visual indication of a location of the item within the at least one rendered x-ray image.

6. The method of claim 1, wherein the automated detection indication includes a label within the at least one rendered x-ray image identifying the item.

7. The method of claim 1, further comprising:
   determining, with the at least one computing device, whether the item contains a threat or does not contain a threat based on the at least one machine-learned model; and
   generating, with the at least one computing device, the automated detection indication when the item contains a threat.

8. The method of claim 7, wherein the automated detection indication includes at least one of a visual indication and an auditory alert when the item contains a threat.

9. The method of claim 1, further comprising:
   determining, with the at least one computing device, whether the item contains a threat or does not contain a threat based on the at least one machine-learned model; and
   generating, with the at least one computing device, the automated detection indication when the item does not contain a threat.

10. The method of claim 1, further comprising:
    transmitting, with the at least one computing device, the automated detection indication to at least one of a baggage handling system or an operator in real-time or near real-time.

11. The method of claim 1, wherein the at least one training data set includes x-ray images of items obtained using an x-ray screening machine.

12. The method of claim 1, wherein the at least one rendered x-ray image is based on scanning at least one object at a security checkpoint in a facility.

13. The method of claim 1, wherein the at least one rendered x-ray image is at least one 2-D projection image.

14. The method of claim 1, wherein the at least one rendered x-ray image is at least one 3-D image of density, stopping power, or atomic composition.

15. The method of claim 1, wherein the first set of x-ray images or the second set of x-ray images include one or more x-ray images having a material information format that identifies items in the image as organic, inorganic or metallic.

16. The method of claim 1, further comprising:
    determining, with the at least one computing device, that the item is a common false-alarm object for explosive detection systems.

17. The method of claim 1, further comprising:
    training, with the at least one computing device, the machine learning algorithm using a result of a previously-executed explosive detection system.

18. A computing-device implemented method for training a model to identify an item in an x-ray image using at least one computing device equipped with a processor, the method comprising:
- receiving a first set of x-ray images of items containing threats, the first set of x-ray images obtained from an x-ray imaging system;
- receiving a second set of x-ray images of items not containing threats, the second set of x-ray images obtained from an x-ray imaging system; and
- training, using the at least one computing device, a machine learning model with at least one training data set of x-ray images, the at least one training data set including the first set of x-ray images of items containing threats and the second set of x-ray images of items not containing threats, wherein the first set of x-ray images or the second set of x-ray images having a material information format that identifies items in the image as organic, inorganic or metallic and the first set of x-ray images or the second set of x-ray images include one or more volumetric x-ray images or one or more projection x-ray images.

19. The method of claim 18, wherein the training includes, determining, with the at least one computing device, at least one forward function of the machine learning model based on the at least one training data set of x-ray images, wherein the forward function is associated with learning a task to analyze the at least one training data set.

20. The method of claim 18, wherein the training includes, determining, with the at least one computing device, a gradient associated with learning the task.

21. A computing-device implemented method for identifying an item in an x-ray image using at least one computing device equipped with a processor, the method comprising:
- executing, using the at least one computing device, at least one machine-learned model, the at least one machine-learned model trained with at least one training data set of x-ray images, the at least one training data set including a first set of x-ray images of items containing threats and a second set of x-ray images of items not containing threats, the first set of x-ray images and the second set of x-ray images comprising whole x-ray images obtained from an x-ray screening system in order to train the at least one machine learned model with whole x-ray images output from the x-ray screening system;
- receiving, with the at least one computing device, at least one rendered x-ray image that includes an item;
- identifying, with the at least one computing device, the item using the at least one model; and
- generating, with the at least one computing device, an automated detection indication associated with the item.

* * * * *